US009962135B2

(12) United States Patent
Yamamoto

(10) Patent No.: US 9,962,135 B2
(45) Date of Patent: *May 8, 2018

(54) TRABECULAR BONE ANALYZER

(71) Applicant: Shimadzu Corporation, Kyoto-shi (JP)

(72) Inventor: Junya Yamamoto, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/197,784

(22) Filed: Jun. 30, 2016

(65) Prior Publication Data

US 2016/0310092 A1 Oct. 27, 2016

Related U.S. Application Data

(63) Continuation of application No. 14/173,325, filed on Feb. 5, 2014, now Pat. No. 9,418,415.

(51) Int. Cl.
| | | |
|---|---|---|
| *A61B 6/00* | (2006.01) | |
| *G06T 7/00* | (2017.01) | |
| *A61B 6/02* | (2006.01) | |
| *G06T 11/00* | (2006.01) | |
| *G06T 7/42* | (2017.01) | |

(52) U.S. Cl.
CPC ............ *A61B 6/505* (2013.01); *A61B 6/025* (2013.01); *A61B 6/4233* (2013.01); *A61B 6/4476* (2013.01); *G06T 7/0012* (2013.01); *G06T 7/42* (2017.01); *G06T 11/003* (2013.01); *G06T 2207/10081* (2013.01);
(Continued)

(58) Field of Classification Search
CPC ....... G06T 7/42; G06T 7/0012; G06T 11/003; G06T 2207/10144; G06T 2207/20104; G06T 2207/30008; G06T 2207/10081; A61B 6/505; A61B 6/4476; A61B 6/4233; A61B 6/025
See application file for complete search history.

(56) References Cited

U.S. PATENT DOCUMENTS

| 4,282,438 A | 8/1981 | Nishida et al. | |
|---|---|---|---|
| 4,698,328 A * | 10/1987 | Neer .................... | A61K 38/29 514/11.8 |

(Continued)

FOREIGN PATENT DOCUMENTS

| JP | 2005-1927657 A | 2/2005 |
|---|---|---|
| JP | 2007-524438 | 8/2006 |

(Continued)

OTHER PUBLICATIONS

Japanese Office Action dated Dec. 18, 2014 for Patent Application No. JP 2011-16683.
(Continued)

*Primary Examiner* — John Strege
(74) *Attorney, Agent, or Firm* — Muir Patent Law, PLLC

(57) ABSTRACT

Disclosed herein is a trabecular bone analyzer that can quantitatively determine the state of trabecular bone accurately. The trabecular bone analyzer of may perform trabecular bone analysis on a tomographic image D. In the tomographic image D, trabeculae forming a network may appear without overlapping. Therefore, such trabecular bone analysis may more accurately quantify trabecular bone.

20 Claims, 6 Drawing Sheets

(52) U.S. Cl.
CPC .............. *G06T 2207/10144* (2013.01); *G06T 2207/20104* (2013.01); *G06T 2207/30008* (2013.01)

(56) References Cited

U.S. PATENT DOCUMENTS

| | | | |
|---|---|---|---|
| 5,915,036 | A | 6/1999 | Grunkin et al. |
| 7,539,332 | B1 * | 5/2009 | Al-Dayeh ................ G06K 9/34 128/922 |
| 7,660,453 | B2 | 2/2010 | Lang |
| 7,664,298 | B2 | 2/2010 | Lang et al. |
| 8,238,521 | B2 | 8/2012 | McKim et al. |
| 8,639,009 | B2 | 1/2014 | Lang et al. |
| 8,965,075 | B2 | 2/2015 | Arnaud et al. |
| 2002/0076090 | A1 | 6/2002 | Lee et al. |
| 2002/0191823 | A1 | 12/2002 | Wehrli et al. |
| 2004/0242987 | A1 | 12/2004 | Liew et al. |
| 2005/0010106 | A1 | 1/2005 | Lang et al. |
| 2007/0253529 | A1 | 11/2007 | Seppi |
| 2010/0111395 | A1 | 5/2010 | Tamakoshi |
| 2010/0266190 | A1 | 10/2010 | Zagorchev et al. |
| 2011/0075793 | A1 | 3/2011 | Akahori et al. |
| 2012/0277571 | A1 | 11/2012 | Cho et al. |

FOREIGN PATENT DOCUMENTS

| | | |
|---|---|---|
| JP | 2011-087917 | 5/2011 |
| WO | WO 2004/086972 A2 | 10/2004 |

OTHER PUBLICATIONS

Yu et al., "Improved total variation-based image reconstruction algorithm for linear scan conebeam computed tomography." Journal of Electronic Imaging, vol. 22, Issue 3, Aug. 19, 2013.
Croucher et al., Assesment of Cancellous Bone Structure: Comparison of Strut Analysis, Trabecular Bone Pattern Factor, and Marrow Space Star Volume. Journal of Bone and Mineral Research, 1996.
Ulrich et al., Finite element analysis of trabecular bone structure: a comparison of image-based meshing techniques, journal of biomechanics, 1998.
Madzin et al., "Measurement of Trabecular Bone Structure using Fractal Analysis." Biomed, 2008, pp. 587-590.
Muller et al., "Non-invasive bone biopsy: a new method to analyze and display the three-dimensional structure of trabecular bone." IOP publishing ltd., 1994.
Feldkamp et al., "The Direct Examination of Three-Dimensional Bone Architecture in vitro by Computed Tomography." Journal of bone and mineral research, 1989.
Elmoutaouakkll et al, "Segmentation of Cancellous Bone from High-Resolution Computed Tomography Images: Influence of Trabecular Bone Measurements." IEEE, 2002.

* cited by examiner

[Fig. 1]
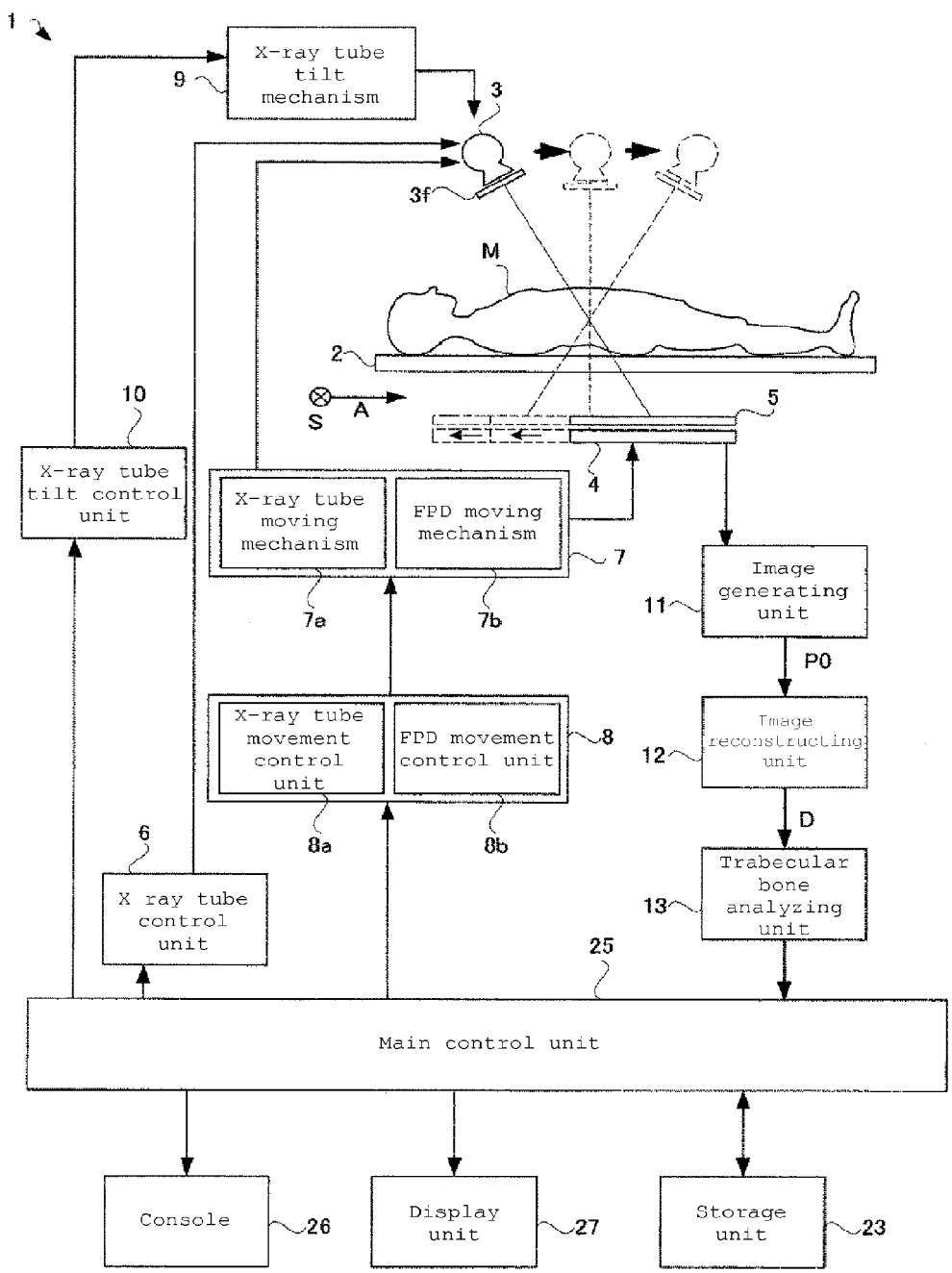

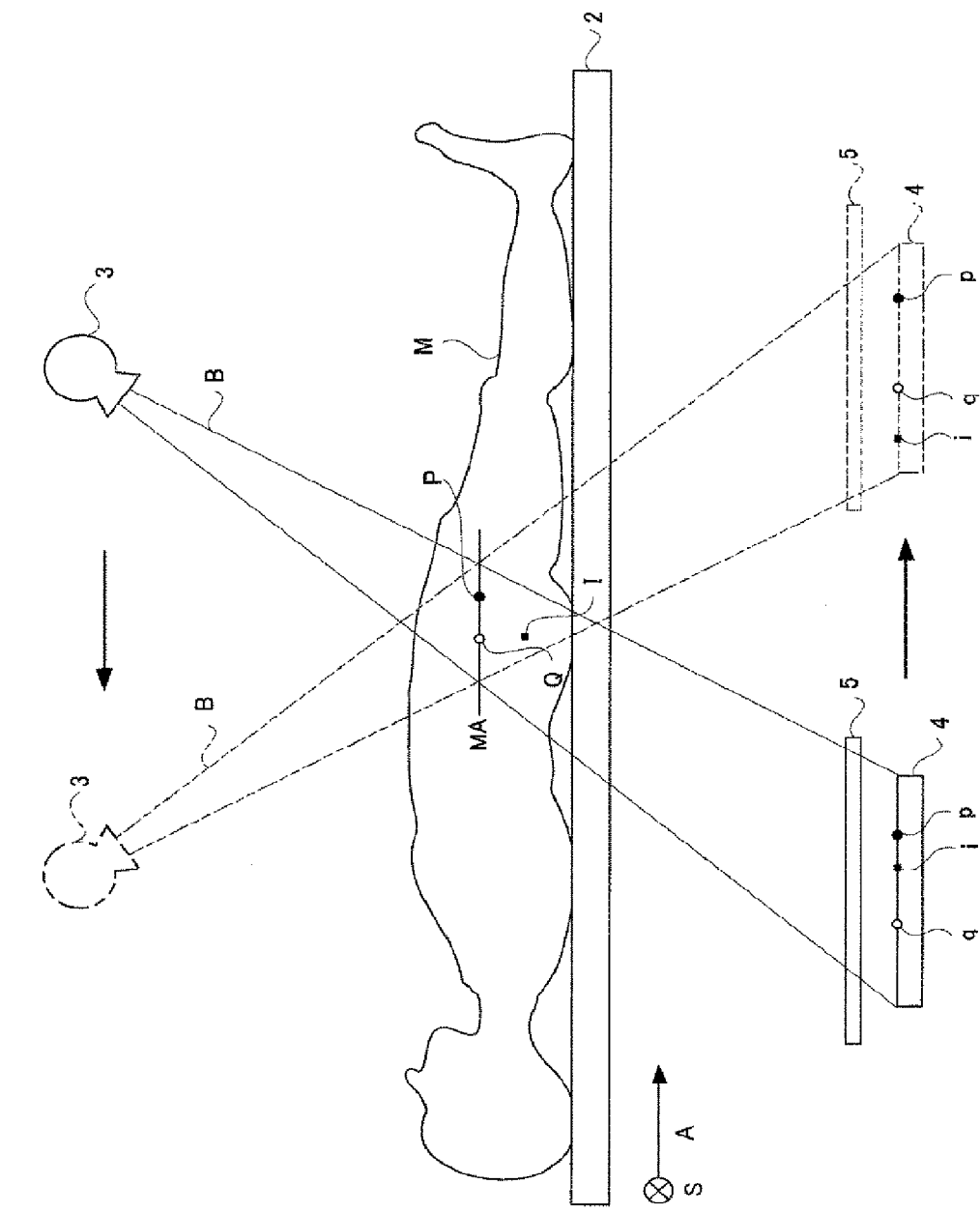
[Fig. 2]

[Fig. 3]
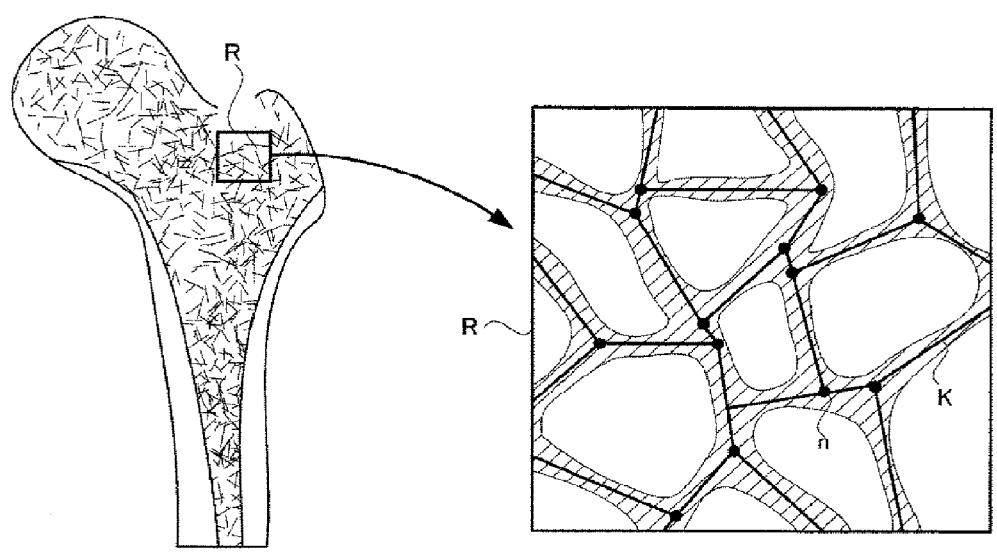
[Fig. 4]
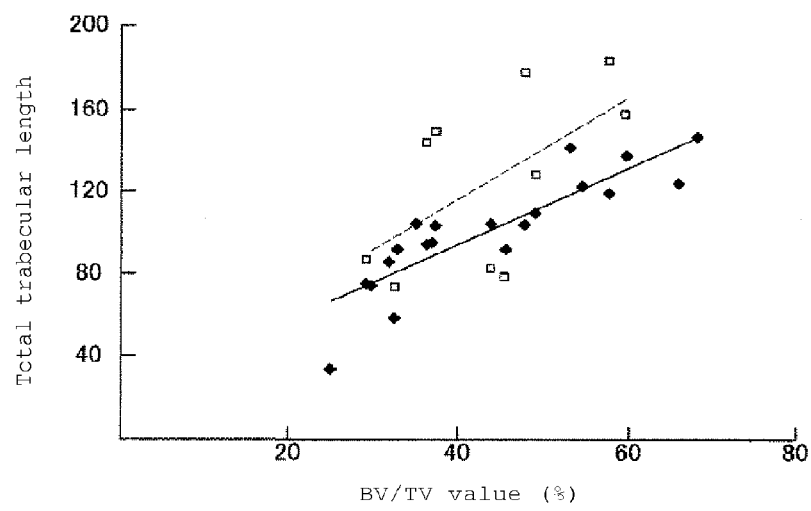

[Fig. 5]
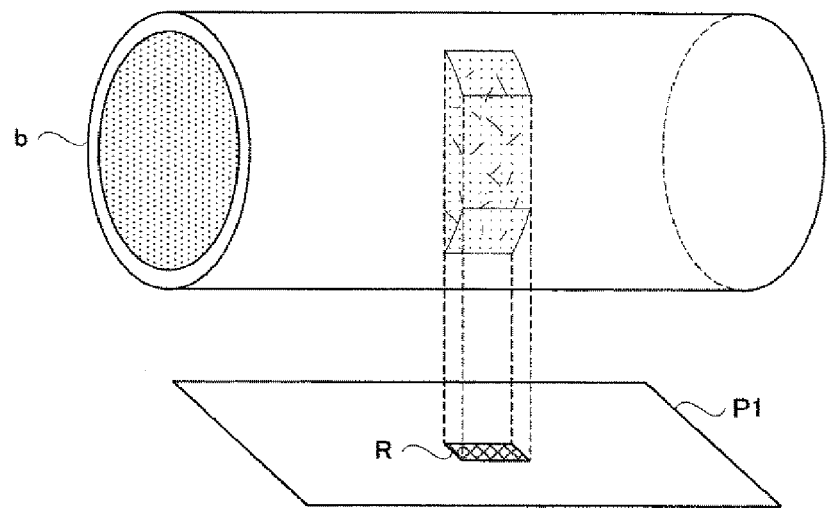
[Fig. 6]
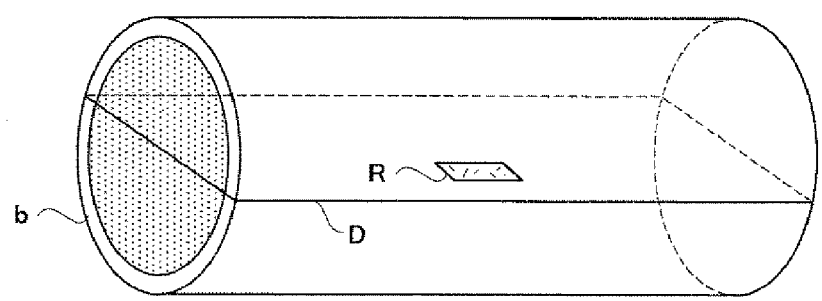

[Fig. 7]
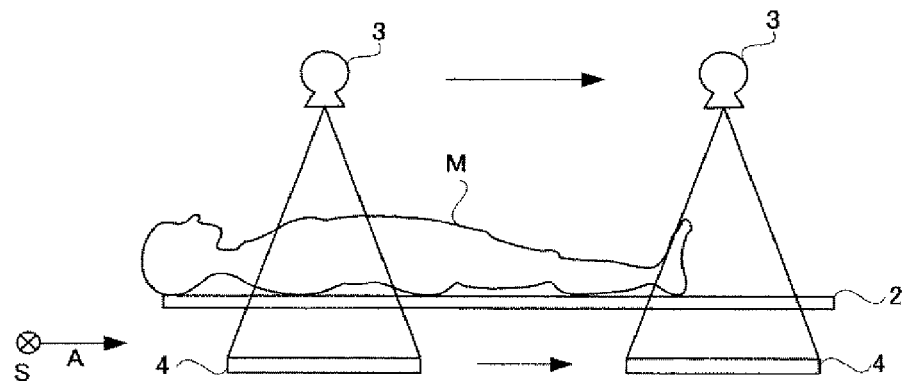
[Fig. 8]
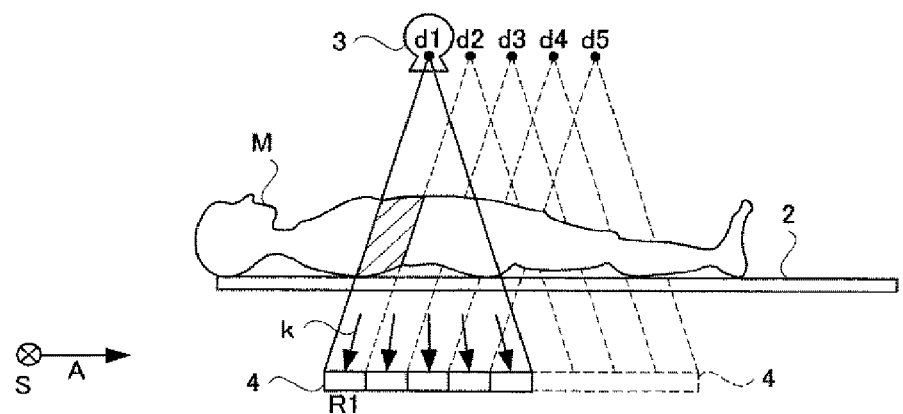
[Fig. 9]
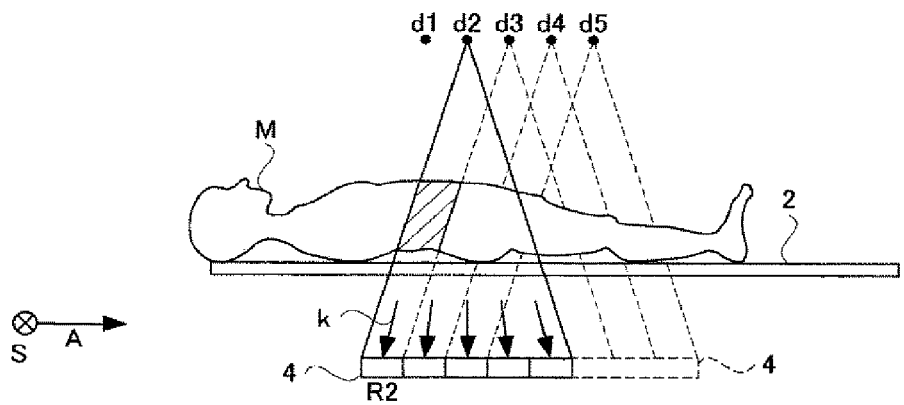

[Fig. 10]
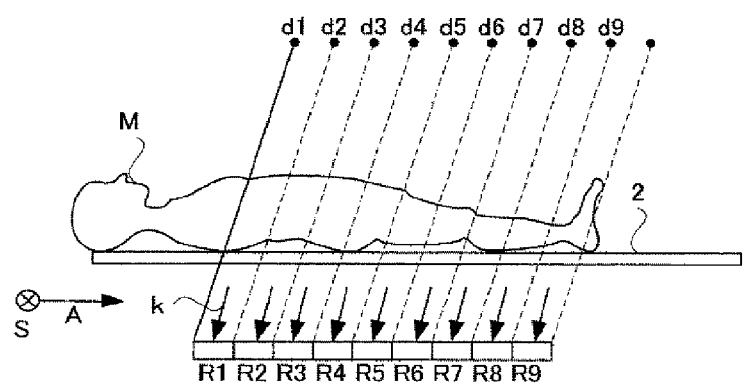
[Fig. 11]
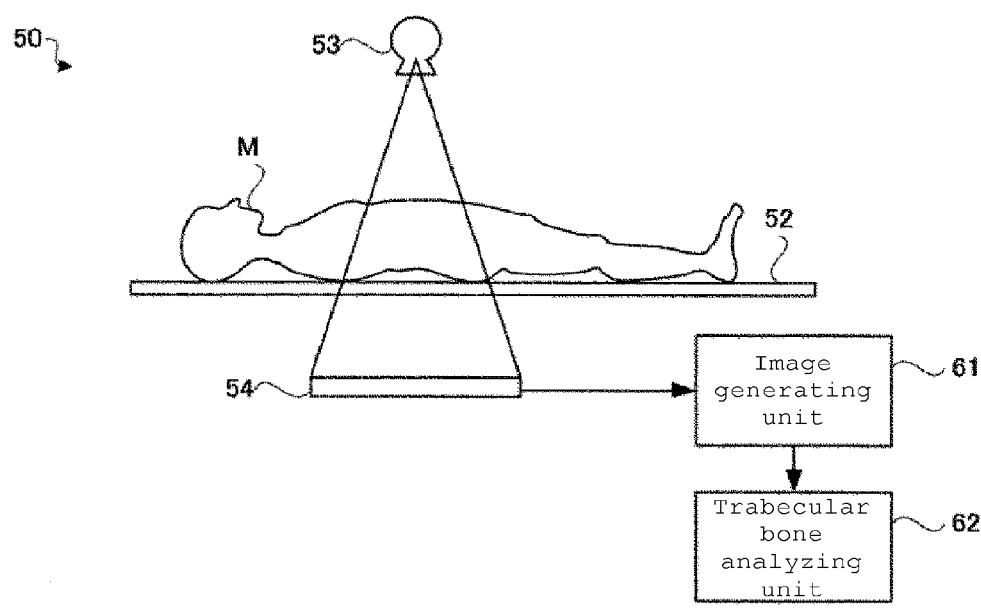

TRABECULAR BONE ANALYZER

CLAIM OF PRIORITY

This application is a Continuation of and claims priority to U.S. patent application Ser. No. 14/173,325 filed on Feb. 5, 2014, the disclosure of which is hereby incorporated by reference herein in its entirety.

BACKGROUND OF THE INVENTION

1. Field of the Invention

The present invention relates to a trabecular bone analyzer for analyzing the trabecular bone of a subject. A trabecular bone analyzer may acquire and analyze a radiation fluoroscopic image of a subject to perform trabecular bone analysis.

2. Description of the Related Art

A trabecula is often a long and thin structure forming a spongy substance inside bones. The health or disease status of a subject M can be checked by determining whether such trabeculae are sufficiently present in a bone. Further, the bone strength of the subject M can be determined by analyzing the trabecular bone of the subject M.

A conventional trabecular bone analyzing method will be described. As shown in FIG. 11, a conventional trabecular bone analyzer 50 includes a top board 52 on which a subject M is to be placed, a radiation source 53 provided above the top board 52, and a detector 54 provided below the top board 52. Trabecular bone analysis is performed on an image acquired by plain radiography performed using such a device as shown in FIG. 11. Plain radiography is a method for taking a fluoroscopic image by irradiating a subject with radiation only once.

A trabecular bone analyzing unit 62 performs trabecular bone analysis to quantify trabecular bone inside a bone. When the thus determined value is low, the amount of trabecular bone is small, which indicates that the bone strength of the subject M is low.

Alternatively, trabecular bone analysis may be performed based on the three-dimensional structure of trabecular bone of a subject acquired by a CT device. That is, this is a method in which a tomographic image is acquired by synchronously rotating a radiation source and a detector once around a subject, and trabecular bone analysis is performed on the tomographic image (see, for example, JP 2005-192657 A).

SUMMARY

However, such conventional methods have the following problem.

That is, the conventional trabecular bone analyzing methods have a problem that trabecular bone cannot be accurately quantified.

In the case of one of the conventional methods, plain radiography is performed by irradiating a subject with radiation only once to acquire a subject image, and trabecular bone analysis is performed on the subject image. In fact, trabeculae form a three-dimensional net-like spongy substance inside bones. Therefore, when conventional plain radiography is performed for the imaging of the structure of trabecular bone, an image in which trabeculae overlap one another is acquired. That is, trabeculae unclearly appear in the acquired fluoroscopic image. Even when trabecular bone analysis is performed based on such an image, trabecular bone cannot be accurately quantified.

On the other hand, in the case in which a tomographic image is taken by a CT device by rotating a radiation source and a detector once around a subject, the acquired tomographic image is inferior in resolution to a fluoroscopic image acquired by plain radiography, and in addition, a wide region of the subject is exposed to radiation. Therefore, even when trabecular bone analysis is performed using a CT device, trabecular bone cannot be accurately and safely quantified.

One reason why the resolution of a CT device is low will be described. A detector in a CT device is provided with a plate-shaped collimator that absorbs a scattered radiation component. This collimator is provided between adjacent detection elements in the detector. In providing the collimator, the size of detection elements of the detector cannot be reduced. When the detection elements are large in size, the pixel size of a tomographic image generated by the CT device also becomes large, and therefore the resolution of the tomographic image is reduced.

The collimator is typically considered necessary for the CT device. This is because when the collimator is eliminated so that a scattered radiation component enters the detector, the CT device cannot accurately calculate CT values, and therefore a clear tomographic image cannot be acquired.

Under the circumstances, it is an object of the present invention to provide a trabecular bone analyzer that can quantitatively determine the state of trabecular bone accurately.

To address limitations of the conventional art, a trabecular bone analyzer according to some embodiments includes: a radiation source that emits radiation; a detector configured to detect radiation that has passed through a subject; a radiation source moving unit configured to move the radiation source in one direction; a radiation source movement control unit configured to control the radiation source moving unit; an image generating unit configured to generate an image based on an output from the detector; an image reconstructing unit configured to generate a tomographic image based on images continuously taken by moving the radiation source with respect to the subject; and a trabecular bone analyzing unit configured to calculate, based on the tomographic image, data for quantitatively determining a state of trabecular bone.

According to some embodiments, it is possible to quantitatively determine the state of trabecular bone more accurately. According to a conventional method, trabecular bone analysis is performed using a fluoroscopic image acquired by plain radiography. Such an analysis cannot always acquire an accurate result. This is because overlapping trabeculae unclearly appear in the fluoroscopic image. On the other hand, according to some embodiments of the present invention, trabecular bone analysis is performed on a tomographic image. In the tomographic image, trabeculae forming a network may clearly appear without overlapping. Therefore, such trabecular bone analysis can more accurately quantify trabecular bone.

Further, as compared to a conventional method in which trabecular bone analysis is performed based on a tomographic image acquired by a CT device, trabecular bone analysis can be accurately performed while the amount of radiation is reduced. Therefore, according to the present invention, it is possible to provide a safer trabecular bone analyzer. Further, the tomographic device according to some embodiments may use a flat panel detector as in the case of a device for plain radiography, and therefore achieves a higher resolution than a CT device.

Further, according to some embodiments, it is easier to change the positions of the radiation source and the detecting unit with respect to the subject as compared to a CT device. This is because a CT device is provided with a gantry for receiving a radiation source and a detecting unit, and therefore the movements of the radiation source and the detecting unit are limited by the gantry. According to some embodiments, it is possible to more easily adjust the size of a subject image appearing in a tomographic image as compared to a CT device.

Further, the trabecular bone analyzer may include a detector moving unit that moves the detecting unit (or detector) synchronously with movement of the radiation source in a direction the same as or opposite to a direction in which the radiation source moves and a detector movement control unit that controls the detector moving unit.

The above-described configuration is an examplary configuration of the trabecular bone analyzer according to the present invention. The present invention is not limited thereto. For example, some embodiments contemplate a configuration in which the detecting unit moves synchronously with the radiation source.

Further, in some embodiments, the data calculated by the trabecular bone analyzing unit is a value representing a total trabecular length that is a total length of trabeculae appearing in a certain range in the tomographic image.

Further, in some embodiments, the data calculated by the trabecular bone analyzing unit is a value representing a trabecular number that is a number of trabeculae in a certain region of interest in the tomographic image.

When the data calculated by the trabecular bone analyzing unit is a total trabecular length that is the total length of trabeculae or a trabecular number that is the number of trabeculae and the value of the total trabecular length or the trabecular number is larger, the bone strength of the subject may be predicted to be higher.

Further, the data calculated by the trabecular bone analyzing unit may be a value representing an average trabecular length that is an average length of trabeculae in a certain region of interest in the tomographic image.

When the data calculated by the trabecular bone analyzing unit is an average trabecular length, the properties of the inside of a bone of the subject may be digitized for comparison.

Further, the data calculated by the trabecular bone analyzing unit is a value representing fractal dimensionality calculated by performing fractal dimension analysis on the tomographic image.

When the data calculated by the trabecular bone analyzing unit is fractal dimensionality, the degree of deviation of the spongy substance of a bone to be examined from a healthy state may be numerically determined by comparison between the values of fractal dimensionality.

Further, the data calculated by the trabecular bone analyzing unit is a value representing distribution of frequency components calculated by performing frequency analysis on the tomographic image.

(When the data calculated by the trabecular bone analyzing unit shows the distribution of frequency components, the density of a spongy substance may be numerically determined.

According to a conventional method, trabecular bone analysis is performed using a fluoroscopic image acquired by plain radiography. Such an analysis cannot always acquire an accurate result. This is because overlapping trabeculae unclearly appear in the fluoroscopic image. Further, it cannot be said that analysis using a CT device achieves a high resolution. On the other hand, according to certain embodiments, trabecular bone analysis is performed on a tomographic image comparable in resolution to a fluoroscopic image acquired by plain radiography. In the tomographic image, trabeculae forming a network may clearly appear without overlapping. Therefore, such trabecular bone analysis may more accurately quantify trabecular bone.

BRIEF DESCRIPTION OF THE DRAWINGS

FIG. 1 is a functional block diagram illustrating the configuration of a trabecular bone analyzer according to Example 1;

FIG. 2 is a schematic diagram illustrating the principle of taking an image with the trabecular bone analyzer according to Example 1;

FIG. 3 is a schematic diagram illustrating the operations of a trabecular bone analyzing unit according to Example 1;

FIG. 4 is a correlation diagram illustrating the effects according to Example 1;

FIG. 5 is a schematic diagram illustrating the effects according to Example 1;

FIG. 6 is a schematic diagram illustrating the effects according to Example 1;

FIG. 7 is a schematic diagram illustrating the principle of taking an image with a trabecular bone analyzer according to Example 2;

FIG. 8 is a schematic diagram illustrating the principle of taking an image with the trabecular bone analyzer according to Example 2;

FIG. 9 is a schematic diagram illustrating the principle of taking an image with the trabecular bone analyzer according to Example 2;

FIG. 10 is a schematic diagram illustrating the principle of taking an image with the trabecular bone analyzer according to Example 2; and FIG. 11 is a schematic diagram illustrating the configuration of a conventional trabecular bone analyzer.

DETAILED DESCRIPTION OF THE PREFERRED EMBODIMENTS

EXAMPLE 1

Hereinbelow, examples of a trabecular bone analyzer according to embodiments of the present invention will be described with reference to the accompanying drawings. It is to be noted that X-rays in the embodiments correspond to one example of radiation in the present invention. It is to be noted that FPD is an abbreviation for flat panel detector (such as a flat panel X-ray detector).

FIG. 1 is a functional block diagram illustrating the configuration of a trabecular bone analyzer according to Example 1. As shown in FIG. 1, the trabecular bone analyzer 1 according to Example 1 includes: a top board 2 on which a subject M as a target for X-ray tomography is to be placed; an X-ray tube 3 provided above the top board 2 (on one surface side of the top board 2) to irradiate the subject M with a cone-shaped X-ray beam; an FPD 4 provided blow the top board 2 (on the other surface side of the top board) to detect an X-ray fluoroscopic image of the subject M; a synchronous moving mechanism 7 that synchronously moves the X-ray tube 3 and the FPD 4 in opposite directions to each other across a site of interest of the subject M so that a central axis of the cone-shaped X-ray beam is always aligned with a central point of the FPD 4; a synchronous movement control unit 8 that controls the synchronous moving mechanism 7; and an X-ray grid 5 provided so as to cover an X-ray detecting surface of the FPD 4 that detects X-rays to absorb scattered X-rays. In this way, the top board 2 is interposed between the X-ray tube 3 and the FPD 4. The X-ray tube 3 corresponds to a radiation source in this example, and the FPD 4 corresponds to a radiation detecting unit in this example.

The synchronous moving mechanism 7 has an X-ray tube moving mechanism 7a that moves the X-ray tube 3 in the direction of a body axis A of the subject M and an FPD moving mechanism 7b that moves the FPD 4 in the direction of the body axis A of the subject M. Further, the synchronous movement control unit 8 has an X-ray tube movement control unit 8a that controls the X-ray tube moving mechanism 7a and an FPD movement control unit 8b that controls the FPD moving mechanism 7b. The X-ray tube moving mechanism 7a corresponds to a radiation source moving unit in this example, and the X-ray tube movement control unit 8a corresponds to a radiation source movement control unit in this example. The FPD moving mechanism 7b corresponds to a detector moving unit in this example, and the FPD movement control unit 8b corresponds to a detector movement control unit in this example.

The X-ray tube 3 is configured to repeatedly irradiate the subject M with a cone-shaped and pulsed X-ray beam under control of an X-ray tube control unit 6. The X-ray tube 3 is equipped with a collimator that collimates an X-ray beam to a pyramidal cone shape. The X-ray tube 3 and the FPD 4 constitute imaging systems 3 and 4 that take an X-ray fluoroscopic image.

The synchronous moving mechanism 7 is configured to move the X-ray tube 3 and the FPD 4 synchronously. The synchronous moving mechanism 7 moves the X-ray tube 3 straight along a straight-line path parallel to the direction of the body axis A of the subject M (along the longitudinal direction of the top board 2) under control of the synchronous movement control unit 8. The direction in which the X-ray tube 3 and FPD 4 move is coincident with the longitudinal direction of the top board 2. In addition, the cone-shaped X-ray beam emitted from the X-ray tube 3 is always emitted toward a site of interest of the subject M during examination, and the emission angle of the X-ray beam is changed, for example, from an initial angle of −20° to a final angle of 20° by changing the angle of the X-ray tube 3. Such a change in the X-ray emission angle is performed by an X-ray tube tilt mechanism 9. An X-ray tube tilt control unit 10 is provided for the purpose of controlling the X-ray tube tilt mechanism 9.

The trabecular bone analyzer 1 according to Example 1 further includes a main control unit 25 that performs overall control of the individual control units 6, 8 and 10 and a display unit 27 that displays a tomographic image D. This main control unit 25 has a CPU and provides the individual control units 6, 8, and 10 and individual units 11, 12, and 13 that will be described later by executing various programs.

This main control unit 25, the individual control units 6, 8, and 10 and individual units 11, 12, and 13 may be comprised of one or more processors or computers configured by software. Console 26, display unit 27 and storage unit 23 may constitute elements of such computer(s). A "computer" refers to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; a web appliance; a telecommunications device with internet access; a tablet personal computer (PC); a personal digital assistant (PDA); application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, or a chip set; a system on a chip (SoC), or a multiprocessor system-on-chip (MPSoC). "Software" refers to prescribed rules to operate a computer. Examples of software may include: software; code segments; instructions; applets; precompiled code; compiled code; interpreted code; computer programs; and programmed logic.

A storage unit 23 stores all data about the control of the trabecular bone analyzer 1 such as parameters associated with the control of the X-ray tube 3. A console 26 is provided to allow an operator to input instructions for various operations of the trabecular bone analyzer 1.

The synchronous moving mechanism 7 moves the FPD 4, provided below the top board 2, straight in the direction of the body axis A of the subject M (in the longitudinal direction of the top board 2) synchronously with the above-described straight movement of the X-ray tube 3. The direction of the movement is opposite to the direction of movement of the X-ray tube 3. That is, the cone-shaped X-ray beam from the X-ray tube 3 whose focal position and emission direction are changed by moving the X-ray tube 3 is always received by the entire X-ray detecting surface of the FPD 4. In this way, the FPD 4 acquires, for example, 74 fluoroscopic images P0 per examination while moving synchronously with the X-ray tube 3 in opposite directions to each other. More specifically, the imaging systems 3 and 4 move in opposite directions from their initial position indicated by a solid line through a position indicated by a dash line to a position indicated by an alternate long and short dash line shown in FIG. 1. That is, a plurality of X-ray fluoroscopic images are taken while the positions of the X-ray tube 3 and the FPD 4 are changed. As described above, since the cone-shaped X-ray beam is always received by the entire X-ray detecting surface of the FPD 4, the central axis of the cone-shaped X-ray beam is always aligned with the central point of the FPD 4 during tomography. Further, the center of the FPD 4 moves straight during tomography, and this movement is opposite in direction to the movement of the X-ray tube 3. That is, the X-ray tube 3 and the FPD 4 move synchronously in opposite directions to each other along the direction of the body axis A.

That is, the synchronous moving mechanism 7 moves the X-ray tube 3 and the FPD 4 synchronously so that the X-ray tube 3 moves toward one end of the top board 2 in the longitudinal direction of the top board 2 and the FPD 4 moves toward the other end of the top board 2 in the longitudinal direction of the top board 2.

An image generating unit 11 is provided downstream of the FPD 4 to generate a fluoroscopic image P0 based on a detection signal outputted from the FPD 4 (see FIG. 1). An image reconstructing unit 12 is further provided downstream of the image generating unit 11 to synthesize the fluoroscopic images P0 to generate a tomographic image D. The image generating unit 11 and/or the image reconstructing unit 12 may be composed of one or more processors configured by software, such as part of a computer comprising the main control unit 25 or constituting separately configured processor(s)/computer(s).

Hereinbelow, the principle of acquiring a tomographic image with the trabecular bone analyzer 1 according to Example 1 will be described. FIG. 2 is a diagram illustrating a method for acquiring a tomographic image with the X-ray radiographic device according to Example 1. The method will be described with reference to, for example, a virtual plane (reference cutting plane MA) parallel to the top board 2 (horizontal to the vertical direction). As shown in FIG. 2, the image generating unit 11 generates a series of fluoroscopic images P0 while the FPD 4 moves synchronously with and in an opposite direction to the X-ray tube 3 according to the emission direction of a cone-shaped X-ray beam B from the X-ray tube 3 so that points P and Q located in the reference cutting plane MA are always projected onto fixed points p and q in the X-ray detecting surface of the FPD 4, respectively. The projected image of the subject M appears in the series of fluoroscopic images P0 while changing its position. The image reconstructing unit 12 reconstructs the series of fluoroscopic images P0 so that images located in the reference cutting plane MA (e.g., the fixed points p and q) are accumulated to image an X-ray tomographic image. On the other hand, a point I not located in the reference cutting plane MA appears as a point i in the series of subject images while changing its projected position in the FPD 4. Unlike the fixed points p and q, such points i blur without forming an image when the X-ray fluoroscopic images are superposed by the image reconstructing unit 12. By superposing the series of fluoroscopic images P0 in this way, an X-ray tomographic image containing only the images located in the reference cutting plane MA of the subject M is obtained. In this way, by simply superposing the fluoroscopic images P0, a tomographic image D of the reference cutting plane MA is obtained.

Further, a similar tomographic image of any cutting plane horizontal to the reference cutting plane MA can also be obtained by changing the settings of the image reconstructing unit 12. The projected position of the above-described point i moves on the FPD 4 during tomography, and the speed of the movement increases as the distance between the point I before projection and the reference cutting plane MA increases. Based on this, the series of acquired subject images are reconstructed while being shifted at given pitches in the direction of the body axis A so that a tomographic image D of a sectional plane parallel to the reference sectional plane MA can be obtained. Such reconstruction of the series of subject images is performed by the image reconstructing unit 12.

The tomographic image D is sent to a trabecular bone analyzing unit 13. The trabecular bone analyzing unit 13 may be composed of one or more processors or computers configured by software, such as part of a computer comprising the main control unit 25, image generating unit 11, and/or the image reconstructing unit 12, or constituting a separately configured processor/computer. The trabecular bone analyzing unit 13 performs various analyses on the tomographic image D to quantify trabecular bone. The thus obtained individual values are used to predict the bone fracture risk of the subject M. Hereinbelow, individual operations performed by the trabecular bone analyzing unit 13 to quantify trabecular bone will be described.

<Calculation of Total Trabecular Length, Trabecular Number, and Average Trabecular Length>

FIG. 3 is a schematic diagram illustrating the operations of the trabecular bone analyzing unit 13. The left-side diagram in FIG. 3 shows a sectional image of a bone of the subject M appearing in the tomographic image D. The trabecular bone analyzing unit 13 recognizes part of a spongy substance inside the bone as an analytical range R. The analytical range R may be set by an operator through the console 26 or may be set by the trabecular bone analyzing unit 13 based on the estimation of position of a spongy substance from the shape of the bone. Alternatively, the trabecular bone analyzing unit 13 may perform trabecular bone analysis on three-dimensional volume data generated by acquiring a plurality of tomographic images D.

The right-side diagram in FIG. 3 is an enlarged diagram of the analytical range R. In the analytical range R, a sectional image of trabeculae appears. These trabeculae form a cancellous/spongy substance. The trabecular bone analyzing unit 13 acquires branch points n of the trabeculae in the analytical range R by image analysis and determines line segments K connecting the branch points n together. The trabecular bone analyzing unit 13 sums the lengths of these line segments K. The thus obtained value is a total trabecular length that is the total length of the trabeculae in the analytical range R. A larger total trabecular length means that more trabeculae are present in the analytical range R, which indicates that the bone appearing in the tomographic image D is less likely to fracture.

Further, the trabecular bone analyzing unit 13 counts the number of the determined line segments K. The thus obtained value is a trabecular number that is the number of the trabeculae in the analytical range R. A larger trabecular number means that more trabeculae are present in the analytical range R, which indicates that the bone appearing in the tomographic image D is less likely to fracture.

Further, the trabecular bone analyzing unit 13 divides the total trabecular length by the trabecular number. The thus obtained value is an average trabecular length that is the average length of the trabeculae in the analytical range R. The average trabecular length serves as an indicator for understanding the characteristics of spongy substance of the bone appearing in the tomographic image D. That is, bones different in average trabecular length differ in how a force is transmitted inside a bone when an impact is given to the bone even when their total trabecular length is the same. By calculating the average trabecular length of individual bones, the difference in physical properties between the bones can be numerically determined.

The trabecular bone analyzing unit 13 performs the same operations on the other analytical ranges R in the tomographic image D to calculate a total trabecular length, a trabecular number, and an average trabecular length for each of the other analytical ranges R. By performing such operations, it is possible to further enhance the reliability of prediction of bone fracture risk based on the respective values of a total trabecular length, a trabecular number, and an average trabecular length.

<Calculation of Fractal Dimensionality>

Further, the trabecular bone analyzing unit 13 can calculate, in addition to the above values, fractal dimensionality from the tomographic image D by fractal dimension analysis. Fractal dimension analysis is used to numerically express, as fractal dimensionality, a tendency that, when a certain image pattern is expanded, a shape similar to the image pattern before expansion appears in an expanded image.

By performing fractal dimension analysis on the tomographic image D, it is possible to calculate a value (fractal dimensionality) representing the overall tendency of a spongy substance formed by fine structures gathering together. Therefore, the degree of deviation of the bone appearing in the tomographic image D from a healthy state can be quantitatively expressed by calculating fractal dimensionality based on the tomographic image D and comparing the fractal dimensionality with the previously-calculated fractal dimensionality of a healthy bone.

The meaning of such an analysis will be described. It is possible to visually recognize the difference between the spongy substance of a healthy bone and the spongy substance of a diseased bone. However, it is difficult to visually determine, by comparison, which of spongy substances is closer to a healthy state. However, fractal dimension analysis makes it possible to acquire a value representing the tendency of the microstructure of a spongy substance and therefore to more quantitatively determine the health degree of the spongy substance.

The trabecular bone analyzing unit 13 performs fractal analysis on the entire spongy substance in the tomographic image D and calculates a single value of fractal dimensionality per tomographic image D.

<Frequency Analysis>

Further, the trabecular bone analyzing unit 13 can calculate, in addition to the above values, the distribution of frequency components from the tomographic image D by frequency analysis. By performing frequency analysis on the tomographic image D, a value representing the intensity of each frequency component of a spongy substance is acquired and a spectrum showing the relationship between frequency and intensity is produced. The health level of a spongy substance appearing in the tomographic image D can be determined by reference to the spectrum. That is, when the high-frequency component of the spectrum has a higher intensity, the spongy substance is more microscopic and trabeculae form a denser network, which indicates that the subject M has a lower risk of bone fracture. The trabecular bone analyzing unit 13 performs frequency analysis on the entire spongy substance in the tomographic image D and calculates a single spectrum per tomographic image D.

FIG. 4 is a graph for comparison between a conventional trabecular bone analyzing method performed by plain radiography and the method according to certain embodiments the present invention. In FIG. 4, a horizontal axis represents the ratio of trabeculae occupying a predetermined space (BV/TV value) calculated based on the 3D data of a spongy substance acquired by a CT device. When this value is 0, no trabeculae are present in the space to be analyzed. Therefore, a higher BV/TV value means that trabeculae are more densely present in a spongy substance. The BV/TV value is determined from a tomographic image acquired by introducing the subject M into a CT device and taking a plurality of images during one rotation of an X-ray tube and an FPD around the subject.

Each plotted point in FIG. 4 represents the relationship between the BV/TV value and the total trabecular length of a certain portion of a spongy substance. An analytical region used for calculation differs from plotted point to plotted point. Further, data plotted by open squares in FIG. 4 is based on the total length of trabeculae determined by the conventional method. That is, the total length of trabeculae indicated by open squares is determined by analyzing a single fluoroscopic image acquired by plain radiography of the subject M.

On the other hand, the total length of trabeculae indicated by solid diamonds in FIG. 4 is determined by the method according to certain embodiments of the present invention. That is, data plotted by solid diamonds is based on the total length of trabeculae determined by analyzing a tomographic image D acquired by subjecting the subject M to tomography using the device described above with reference to FIG. 1. In order to compare accuracy between the two methods, the BV/TV value indicated by open squares and the BV/TV value indicated by solids diamonds are calculated by the same method. A dash line in FIG. 4 represents the result of first-order approximation of plotted data (open squares) obtained by the conventional method, and a solid line in FIG. 4 represents the result of first-order approximation of plotted data (black diamonds) obtained by the method according to certain embodiments of the present invention.

As can be seen from FIG. 4, variations in data obtained by the method according to certain embodiments are smaller than those obtained by the conventional method. That is, the method according to certain embodiments may determine the total length of trabeculae more accurately than the conventional method.

As shown in FIG. 5, in the conventional method using plain radiography, the analysis of the total length of trabeculae is performed on an analytical region R on a fluoroscopic image P1. In this analytical region R, all the trabeculae contained in a shaded three-dimensional region of a bone b shown in FIG. 5 appear due to plain radiography and therefore overlap one another. That is, a trabecular network does not appear in the analytical region R, which makes it difficult to analyze the total length of trabeculae.

On the other hand, as shown in FIG. 6, in the method according to embodiments using tomography, the analysis of the total length of trabeculae is performed on an analytical region R on a tomographic image D. In this analytical region R, the cross section of a spongy substance, that is, the network structure of trabeculae in a spongy substance appears. Therefore, the analysis of the total length of trabeculae is easily performed and the total length of trabeculae can be more accurately acquired. It is to be noted that the analysis of the total length of trabeculae has been described above with reference to FIGS. 5 and 6, but the same applies to the other quantitative analyses.

<Operations of Trabecular Bone Analyzer>

Hereinbelow, exemplary operations of the trabecular bone analyzer will be described. The following description will be made with reference to a case where the trabecular bone analysis of a living body is performed by the above-described trabecular bone analyzer. In order to analyze the trabecular bone of a subject M with the trabecular bone analyzer, first, the subject M is placed on the top board 2. When an operator instructs the trabecular bone analyzer through the console 26 to acquire a tomographic image, the moving mechanisms 7a and 7b move the X-ray tube 3 and the FPD 4, respectively, synchronously in opposite directions so that 74 fluoroscopic images P0 are continuously taken. The acquired fluoroscopic images P0 are sent to the image reconstructing unit 12 to generate a tomographic image D. The tomographic image D is sent to the trabecular bone analyzing unit 13.

The trabecular bone analyzing unit 13 performs various trabecular bone analyses on the tomographic image D, and results are sent to the display unit 27. Values representing the results of the trabecular bone analyses are displayed on the display unit 27 to complete the operations of the trabecular bone analyzer.

As described above, according to embodiments of the present invention, the state of trabecular bone can be quantitatively determined more accurately. According to a conventional trabecular bone analyzing method, trabecular bone analysis is performed using a fluoroscopic image acquired by plain radiography. Such an analysis cannot always acquire an accurate result. This is because overlapping trabeculae unclearly appear in the fluoroscopic image. However, according to some embodiments, trabecular bone analysis is performed on a tomographic image. In the tomographic image, trabeculae forming a network clearly appear without overlapping. Therefore, such trabecular bone analysis can more accurately quantify trabecular bone.

Further, as compared to a conventional method in which trabecular bone analysis is performed based on a tomographic image acquired by a CT device, trabecular bone analysis can be accurately performed while the amount of radiation is reduced. Therefore, according to embodiments of the present invention, it is possible to provide a safer trabecular bone analyzer. Further, the tomographic device according to some embodiments can use a flat panel detector as in the case of a device for plain radiography, and therefore achieves a higher resolution than a CT device.

Further, it is easier to change the positions of the X-ray tube 3 and the FPD 4 with respect to the subject M as compared to a CT device. This is because a CT device is provided with a gantry for receiving an X-ray tube and an FPD, and therefore the movements of the X-ray tube and the FPD are limited by the gantry. According to some embodiments, it is possible to more easily adjust the size of a subject image appearing in a tomographic image as compared to a CT device.

As described above, when the data calculated by the trabecular bone analyzing unit 13 is a total trabecular length that is the total length of trabeculae or a trabecular number that is the number of trabeculae and the value of the total trabecular length or the trabecular number is larger, the bone fracture risk of the subject M can be predicted to be lower.

Further, as described above, when the data calculated by the trabecular bone analyzing unit 13 is an average trabecular length, the properties of the inside of a bone of the subject M may be digitized for comparison.

Further, when the data calculated by the trabecular bone analyzing unit 13 is fractal dimensionality, the degree of deviation of the spongy substance of a bone to be examined from a healthy state may be numerically determined by comparison between the values of fractal dimensionality.

When the data calculated by the trabecular bone analyzing unit 13 shows the distribution of frequency components, the density of a spongy substance may be numerically determined.

EXAMPLE 2

Hereinbelow, a trabecular bone analyzer according to Example 2 will be described. As shown in FIG. 7, the trabecular bone analyzer according to Example 2 is configured so that a tomographic image can be taken by moving an X-ray tube 3 and an FPD 4 in the direction of a body axis A of a subject M with their positional relationship being maintained. Asynchronous moving mechanism 7 moves the X-ray tube 3 and the FPD 4 synchronously so that the X-ray tube 3 moves toward one end of a top board 2 in the longitudinal direction of the top board 2 and the FPD 4 moves toward one end of the top board 2 in the longitudinal direction of the top board 2.

The configuration of the X-ray radiographic device according to Example 2 is the same as that shown in the functional block diagram of FIG. 1. The configuration of Example 2 is different from that of Example 1 shown in FIG. 1 in that the FPD 4 moves while following the X-ray tube 3 (see FIG. 7) and the X-ray tube 3 does not tilt. Therefore, Example 2 does not always need the X-ray tube tilt mechanism 9 and the X-ray tube tilt control unit 10 shown in FIG. 1.

The principle of taking a tomographic image with the trabecular bone analyzer according to Example 2 will be described. First, as shown in FIG. 7, the imaging systems 3 and 4 move with respect to the subject M with their relative positions being maintained while the subject M is intermittently irradiated with X-rays. That is, the X-ray tube 3 moves in the direction of the body axis A of the subject M after each irradiation, and then again emits X-rays. In this way, a plurality of fluoroscopic images are acquired, and images obtained by processing the fluoroscopic images (long fluoroscopic images that will be described later) are reconstructed into a tomographic image by a filtered back projection method. In the completed tomographic image, a sectional image of the subject M in a certain cutting plane appears.

In order to generate a tomographic image, fluoroscopic images of the subject M taken from different directions are required. The trabecular bone analyzer according to Example 2 generates such images by dividing obtained fluoroscopic images and connecting the divided images. Hereinbelow, this operation will be described. FIG. 8 shows the position of the FPD 4 when a focal point from which X-rays from the X-ray tube 3 are emitted is located at a position d1. During tomography, every time the X-ray tube 3 and the FPD 4 move with respect to the top board 2 in the direction of the body axis A of the subject M by ⅕ of the width of the FPD 4, a fluoroscopic image is taken.

X-rays are radially emitted from the X-ray tube 3 and reach the FPD 4. Therefore, when a generated fluoroscopic image is divided into five segments along the direction of the body axis A of the subject M, as indicated by arrows, the angle of incidence of the X-rays on the FPD 4 is different among the segments. Attention is focused on one of the directions k. The X-rays travelling in this direction k pass through a shaded portion of the subject M and then enter the FPD 4, and therefore the shaded portion of the subject M appears in the segment of the FPD 4 in which the X-rays in the direction k enter. A part of the fluoroscopic image corresponding to this segment is defined as a fragment R1.

FIG. 9 shows the position of the FPD 4 when the focal point from which X-rays from the X-ray tube 3 are emitted is located at a position d2 shifted from the position d1 by ⅕ of the width of the FPD 4. Also at this time during tomography, the positional relationship between the X-ray tube 3 and the FPD 4 is not changed, and therefore the FPD 4 is supposed to have a segment in which X-rays travelling in the direction k enter, and a shaded portion of the subject M appears in the segment of the FPD 4 in which the X-rays in the direction k enter. A part of a fluoroscopic image corresponding to this segment is defined as a fragment R2.

When a comparison is made between the fragment R1 and the fragment R2, the fragment R1 and the fragment R2 are different in a portion of the subject M appearing therein, because the position of the subject M with respect to the imaging systems 3 and 4 is different. When imaging is performed 9 times by changing the focal point from d1 to d9 by shifting the X-ray tube 3 by ⅕ of the width of the FPD 4, different portions of the subject M appear respectively in the fragments R1 to R9 of fluoroscopic images corresponding to the segment of the FPD 4 in which X-rays in the direction k enter. Therefore, as shown in FIG. 10, the fragments R1 to R9 of the fluoroscopic images are connected together in this order along the direction of the body axis A of the subject M to obtain an image taken by irradiating the entire body of the subject M with X-rays from a certain direction k. This image is called as a long fluoroscopic image.

In the trabecular bone analyzer according to Example 2, long fluoroscopic images taken from directions other than the direction k are also generated by the image reconstructing unit 12. Then, the image reconstructing unit 12 generates, based on the long fluoroscopic images different in a direction in which the subject M is projected, a tomographic image of the subject M in a predetermined cutting position.

The operations of the trabecular bone analyzer according to Example 2 are the same as those of the analyzer according to Example 1, and therefore will not be repeatedly described.

As described above, the trabecular bone analyzer according to Example 2 is configured to acquire a tomographic image D from long fluoroscopic images acquired by virtually performing slot radiography. By performing radiography in such a manner as described above, it is possible to provide a radiographic device that can acquire a wide range tomographic image.

The present invention is not limited to the above-described configurations, and can be modified. For example, the following modifications are contemplated:

(1) In some embodiments, the trabecular bone analyzer may be configured to previously acquire the relationship between a BV/TV value and a total trabecular length shown in FIG. 4 to acquire a BV/TV value corresponding to a total trabecular length calculated by the trabecular bone analyzing unit 13. This makes it possible to estimate the three-dimensional structure of trabecular bone by tomography.

(2) The above-described examples are medical devices, but the present invention can be applied also to industrial or nuclear devices.

(3) X-rays in the above-described examples are one example of radiation in the present invention. However, the present invention can be applied to radiation other than X-rays.

What is claimed is:

1. A trabecular bone analyzer comprising:
a radiation source configured to emit radiation;
a flat panel detector to detect radiation that has passed through a subject;
a radiation source moving unit configured to move the radiation source in one direction;
a radiation source movement control unit configured to control the radiation source moving unit;
an image generating unit configured to generate an image based on an output from the flat panel detector;
an image reconstructing unit configured to generate a 2-dimensional tomographic image by superposing images continuously taken by moving the radiation source with respect to the subject;
a trabecular bone analyzing unit configured to calculate, based on the 2-dimensional tomographic image, data for quantitatively determining a state of trabecular bone; and
means for estimating a ratio of trabecular bone that occupies a predetermined 3-dimensional space obtained from the data calculated by the trabecular bone analyzing unit.

2. The trabecular bone analyzer according to claim 1, further comprising:
a detector moving unit configured to move the flat panel detector synchronously with movement of the radiation source in a direction the same as or opposite to a direction in which the radiation source moves; and
a detector movement control unit configured to control the detector moving unit.

3. The trabecular bone analyzer according to claim 1, wherein
the data calculated by the trabecular bone analyzing unit is a value representing a total trabecular length that is a total length of trabeculae in a certain region of interest in the 2-dimensional tomographic image.

4. The trabecular bone analyzer according to claim 1, wherein
the data calculated by the trabecular bone analyzing unit is a value representing a trabecular number that is the number of trabeculae in a certain region of interest in the 2-dimensional tomographic image.

5. The trabecular bone analyzer according to claim 1, wherein
the data calculated by the trabecular bone analyzing unit is a value representing an average trabecular length that is an average length of trabeculae in a certain region of interest in the 2-dimensional tomographic image.

6. The trabecular bone analyzer according to claim 1, wherein
the data calculated by the trabecular bone analyzing unit is a value representing fractal dimensionality calculated by performing fractal dimensional analysis on the 2-dimensional tomographic image.

7. The trabecular bone analyzer according to claim 1, wherein
the data calculated by the trabecular bone analyzing unit is a value representing distribution of frequency components calculated by performing frequency analysis on the 2-dimensional tomographic image.

8. The trabecular bone analyzer according to claim 2, wherein
the data calculated by the trabecular bone analyzing unit is a value representing a total trabecular length that is a total length of trabeculae in a certain region of interest in the 2-dimensional tomographic image.

9. The trabecular bone analyzer according to claim 2, wherein
the data calculated by the trabecular bone analyzing unit is a value representing a trabecular number that is the number of trabeculae in a certain region of interest in the 2-dimensional tomographic image.

10. The trabecular bone analyzer according to claim 2, wherein
the data calculated by the trabecular bone analyzing unit is a value representing an average trabecular length that is an average length of trabeculae in a certain region of interest in the 2-dimensional tomographic image.

11. The trabecular bone analyzer according to claim 2, wherein
the data calculated by the trabecular bone analyzing unit is a value representing fractal dimensionality calculated by performing fractal dimensional analysis on the 2-dimensional tomographic image.

12. The trabecular bone analyzer according to claim 2, wherein
the data calculated by the trabecular bone analyzing unit is a value representing distribution of frequency components calculated by performing frequency analysis on the tomographic image.

13. A trabecular bone analyzer comprising:
a radiation source configured to emit radiation at a discrete number of exposure periods;
a radiation source moving unit configured to move the radiation source in a first direction;

a radiation source tilt unit configured to tilt the radiation source and change a radiation emission angle for each of the discrete number of exposure periods;

a flat panel detector to detect radiation that has passed through a subject at each of the discrete number of exposure periods;

a detector moving unit configured to move the flat panel detector in a second direction synchronously with movement of the radiation source, wherein a value of the radiation emission angle changes in accordance with the movement of the flat panel detector and the movement of the radiation source;

an image generating unit configured to generate images based on radiation detected by the flat panel detector at each of the discrete number of exposure periods;

an image reconstructing unit configured to generate a 2-dimensional tomographic image by superposing the images generated by the image generating unit;

a trabecular bone analyzing unit configured to calculate, based on the 2-dimensional tomographic image, data for quantitatively determining a state of trabecular bone; and means for estimating a ratio of trabecular bone that occupies a predetermined 3-dimensional space obtained from the data calculated by the trabecular bone analyzing unit.

14. The trabecular bone analyzer according to claim 13, further comprising:

a radiation source movement control unit configured to control the radiation source moving unit.

15. The trabecular bone analyzer according to claim 13, further comprising:

a detector movement control unit configured to control the detector moving unit.

16. The trabecular bone analyzer according to claim 13, further comprising:

a radiation source tilt control unit configured to control the radiation source tilt unit.

17. A trabecular bone analyzer comprising:

a radiation source configured to emit radiation at a discrete number of intermittent periods;

a radiation source moving unit configured to move the radiation source in a linear direction along an axis of a subject;

a detector configured to detect radiation that has passed through the subject at the discrete number of intermittent periods;

a detector moving unit configured to move the detector synchronously with movement of the radiation source in the linear direction and maintain a consistent distance between the radiation source and the detector;

an image generating unit configured to generate images based on radiation detected at each of the discrete number of intermittent periods by the detector as the radiation source and the detector move in the linear direction;

a long image generating unit configured to divide each of the images into a plurality of image sections according to an angle of incidence of radiation and connect image sections having a same angle of incidence of radiation to form multiple long images along the axis of the subject;

an image reconstructing unit configured to generate a 2-dimensional tomographic image by superposing the multiple long images by the long image generating unit;

a trabecular bone analyzing unit configured to calculate, based on the 2-dimensional tomographic image, data for quantitatively determining a state of trabecular bone; and means for estimating a ratio of trabecular bone that occupies a predetermined 3-dimensional space obtained from the data calculated by the trabecular bone analyzing unit.

18. The trabecular bone analyzer according to claim 17, wherein each of the multiple long images has an angle of incidence of radiation that is different from others of the multiple long images.

19. The trabecular bone analyzer according to claim 17, wherein each of the images generated by the image generating unit corresponds to a portion of an image plane along the axis of the subject.

20. The trabecular bone analyzer according to claim 1, wherein the trabecular bone analyzing unit is configured to determine segment lengths as represented in the 2-dimensional tomographic image of segments of trabeculae identified in a certain region of interest of the 2-dimensional tomographic image, and to calculate, based on the determined segment lengths, the data used by the means for estimating.

* * * * *